US00PP29678P2

(12) United States Plant Patent
Oltmanns

(10) Patent No.: US PP29,678 P2
(45) Date of Patent: Sep. 18, 2018

(54) ***THUJA* PLANT NAMED 'KING OF BRABANT'**

(50) Latin Name: *Thuja occidentalis*
Varietal Denomination: King of Brabant

(71) Applicant: Wilfried Oltmanns, Edewecht (DE)

(72) Inventor: Wilfried Oltmanns, Edewecht (DE)

(73) Assignee: Van Vliet New Plants B.V., Stroe (NL)

( * ) Notice: Subject to any disclaimer, the term of this patent is extended or adjusted under 35 U.S.C. 154(b) by 18 days.

(21) Appl. No.: 15/530,647

(22) Filed: Feb. 13, 2017

(51) Int. Cl.
*A01H 7/00* (2006.01)

(52) U.S. Cl.
USPC ..... Plt./213

(58) Field of Classification Search
USPC ..... Plt./213
CPC ..... A01H 7/00
See application file for complete search history.

*Primary Examiner* — Keith O Robinson
(74) *Attorney, Agent, or Firm* — Penny J. Aguirre

(57) ABSTRACT

A new cultivar of *Thuja occidentalis* named 'King of Brabant' that is characterized by its very compact and tight plant habit, its straight upright, pyramidal plant shape and its vigorous growth habit for having a compact plant habit.

2 Drawing Sheets

Botanical classification: *Thuja occidentalis.*
Varietal denomination: 'King of Brabant'.

BACKGROUND OF THE INVENTION

The present invention relates to a new and distinct cultivar of *Thuja occidentalis* and will be referred to hereafter by its cultivar name, 'King of Brabant'. 'King of Brabant' represents a new cultivar of northern white cedar, an evergreen tree grown for landscape use and particularly useful for hedging.

The inventor discovered 'King of Brabant' as a naturally occurring branch mutation of 'Brabant' (not patented) that was growing in a field at his nursery in summer of 2008 in Edewecht, Germany.

Asexual propagation of the new cultivar was first accomplished by the Inventor using stem cuttings in Edewecht, Germany in January of 2010. Asexual propagation by stem cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'King of Brabant' as a unique cultivar of *Thuja.*

1. 'King of Brabant' exhibits a very compact and tight plant habit.
2. 'King of Brabant' exhibits a straight upright, pyramidal plant shape.
3. 'King of Brabant' exhibits a vigorous growth habit for having a compact plant habit.

The parent plant of 'King of Brabant', 'Brabant', differs from 'King of Brabant' in having a more open and les consistent plant habit and a less upright plant shape. 'King of Brabant' can be most closely compared to the *Thuja plicata* cultivars 'Aurescens' (not patented) and 'Gelderland' (not patented). 'Aurescens' is similar to 'King of Brabant' in having a vigorous growth habit, foliage that is green in color and winter hardiness. 'Aurescens' differs from 'King of Brabant' in having a much less compact and less tight plant habit and foliage that fades to a bronze brown color in the winter. 'Gelderland' is similar to 'King of Brabant' in foliage color and plant vigor. 'Gelderland' differs from 'King of Brabant' in having a much less compact growth habit, less pyramidal shape and coarser foliage.

BRIEF DESCRIPTION OF THE DRAWINGS

The accompanying colored photographs illustrate the overall appearance and distinct characteristics of the new *Thuja*. The photographs were taken of a six year-old plant as grown outdoors in 40-cm circular containers in Stroe, The Netherlands.

Figure 1:
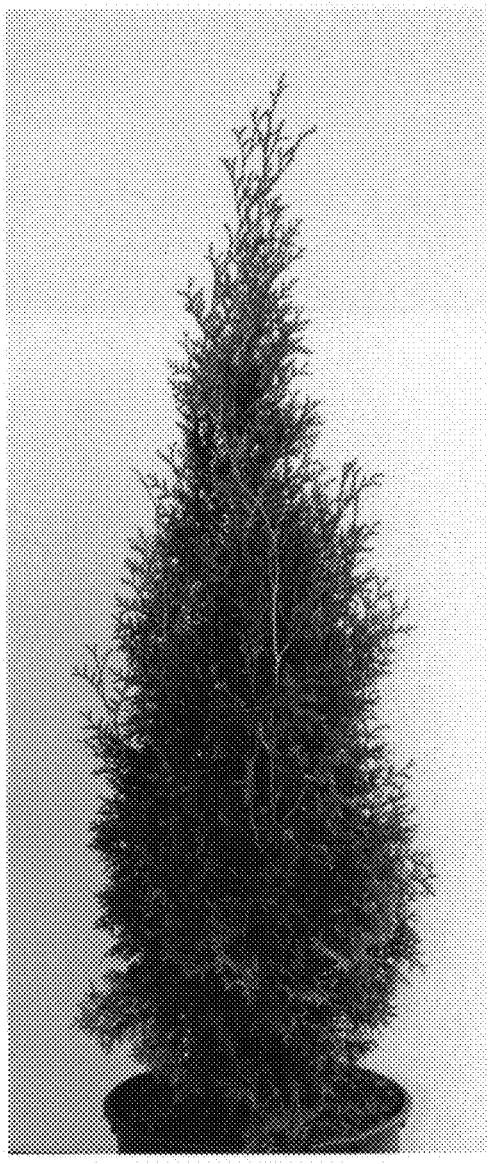
FIG. 1 provides an overall view of the habit of 'King of Brabant'.
Figure 2:
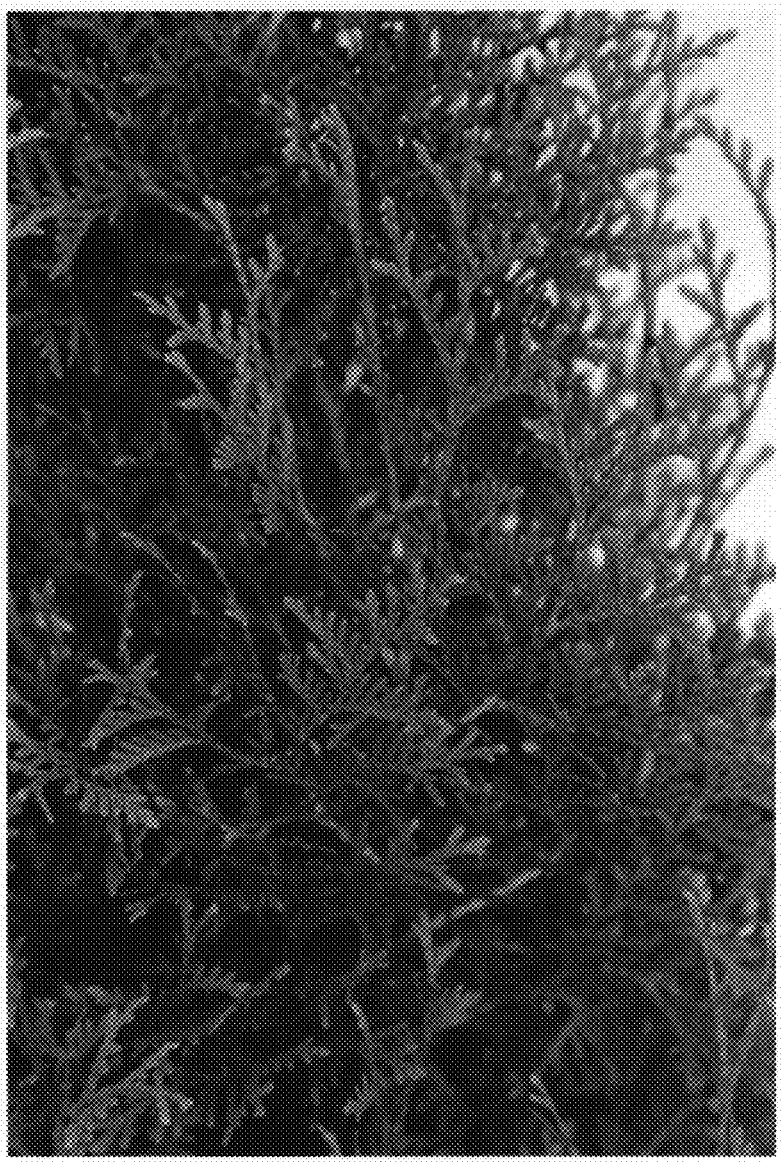
FIG. 2 provides a close-up view of the foliage of 'King of Brabant'.

The colors in the photographs are as close as possible with the photographic and printing technology utilized and the color values cited in the detailed botanical description accurately describe the colors of the new *Thuja.*

DETAILED BOTANICAL DESCRIPTION

The following is a detailed description of the new cultivar as taken from six year-old plants as grown outdoors in 40-cm circular containers in Stroe, The Netherlands with average day temperatures ranging from 14° to 26° C. and average night temperatures ranging from 4° to 16° C. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Plant type.*—Coniferous, evergreen tree.

*Plant habit.*—Narrow conical, upright and compact.

*Plant size.*—An average of 145 cm in height and 55 cm in width as a six year-old plant in a container.

*Cold hardiness.*—At least to U.S.D.A. Zone 3.

*Diseases and pests.*—No susceptibility or resistance to diseases or pests has been observed.

*Root description.*—Fibrous, moderately branched, moderately thick, about 174A in color.

*Propagation.*—Stem cuttings.

*Growth rate.*—Vigorous for a compact cultivar, an average of 30 cm per season.

*Root development.*—A rooted cutting is produced in about 4 weeks, a plant 80 to 100 cm in height can be obtained in 3 years from a rooted cutting.

Branch description:

*Branch quantity.*—Average of 66 lateral branches, multi-branched from base (no trunk).

*Branch shape.*—Rounded.

*Branch size.*—Average of 65.5 cm in length and 8 mm in diameter.

*Branch surface.*—Covered with scale-like leaves that are glossy and glabrous.

*Branching.*—Very freely branching.

*Branch arrangement.*—Alternate.

*Branch strength.*—Strong.

*Internode length.*—Average of 1.9 cm.

*Branch color.*—Young branches; a color between 143A and 144A, one-year old stems; a blend of 164C, 167B and N167B, older bark; 200A to 200B.

Foliage description:

*Leaf arrangement.*—Opposite.

*Leaf attachment.*—Sessile.

*Leaf shape.*—Linear, scale-like.

*Leaf division.*—Simple.

*Leaf base.*—Cuneate.

*Leaf apex.*—Short apiculate.

*Leaf venation.*—Not distinguishable, coloration matches leaf coloration.

*Leaf margins.*—Entire.

*Leaf fragrance.*—When crushed, scale-like leaves produce a very strong pleasant smell typical fragrance of *Thuja occidentalis.*

*Leaf surface.*—Upper and lower surfaces; glabrous and glossy.

*Leaf color.*—Immature upper surface; 144A, immature lower surface; 144B, mature upper surface; color between NN137B and 147A, mature lower surface; 137A.

*Leaf size.*—2.6 to 3.5 cm in length and 1.5 mm in width.

*Leaf quantity.*—Average of over 10,000 scale-like leaves per branch.

*Leaf glands.*—Average of 0.5 mm in diameter, orbicular in shape, color between NN137B and 147A on upper side, 137A on lower side.

Cone description: Neither male nor female cones have been observed to date.

It is claimed:

1. A new and distinct cultivar of *Thuja* plant named 'King of Brabant' as herein illustrated and described.

* * * * *